United States Patent

Polansky

[11] Patent Number: 5,705,496
[45] Date of Patent: Jan. 6, 1998

[54] CRYSTALLINE BENZATHINE SALT OF CEFONICID AND ITS PREPARATION

[75] Inventor: Theodore John Polansky, Harleysville, Pa.

[73] Assignee: SmithKline Beecham Corporation, Philadelphia, Pa.

[21] Appl. No.: 522,386

[22] PCT Filed: Mar. 24, 1994

[86] PCT No.: PCT/US94/03235

§ 371 Date: Sep. 25, 1995

§ 102(e) Date: Sep. 25, 1995

[87] PCT Pub. No.: WO94/21649

PCT Pub. Date: Sep. 29, 1994

[51] Int. Cl.$^6$ .......................... A61K 31/545; C07D 501/36
[52] U.S. Cl. ...................... 514/204; 540/226; 540/227
[58] Field of Search ...................... 514/204; 540/226, 540/227

[56] References Cited

U.S. PATENT DOCUMENTS

| 4,048,311 | 9/1977 | Berges | 424/246 |
| 4,576,937 | 3/1986 | Polansky | 514/204 |
| 4,737,492 | 4/1988 | Gerson et al. | 514/204 |
| 5,276,024 | 1/1994 | Schneider et al. | 514/202 |

FOREIGN PATENT DOCUMENTS

| 0 154 484 | 8/1986 | European Pat. Off. | C17D 501/36 |
| 0 399 094 | 3/1992 | European Pat. Off. | C07D 501/36 |
| WO 87/03876 | 7/1987 | WIPO | C07D 501/34 |
| WO 92/17600 | 10/1992 | WIPO | C12P 17/18 |

*Primary Examiner*—Mukund J. Shah
*Assistant Examiner*—Pavanaram K. Sripada
*Attorney, Agent, or Firm*—Wayne J. Dustman; Charles M. Kinzig; Edward T. Lentz

[57] ABSTRACT

The present invention relates to benzathine salts of cefonicid, a member of the cephalosporin family of antibiotics, which are crystalline.

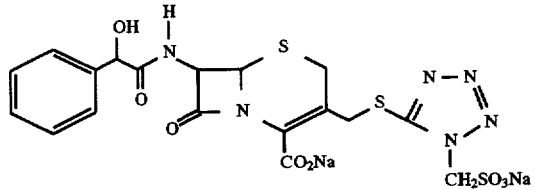

8 Claims, No Drawings

CRYSTALLINE BENZATHINE SALT OF CEFONICID AND ITS PREPARATION

FIELD OF THE INVENTION

The present invention relates to benzathine salts of cefonicid, a member of the cephalosporin family of antibiotics.

BACKGROUND

Cefonicid is a cephalosporin antibiotic presently used as a parenterally administered drug in the treatment of bacterial infections. Cefonicid, whose chemical name is 7-D-mandelamido-3-(1-sulfomethyltetrazol-5-yl)-thiomethyl-3-cephem-4-carboxylic acid, was first disclosed within a large generic class of compounds disclosed and claimed in U.S. Pat. No. 4,048,311. The structure of the disodium salt of cefonicid is:

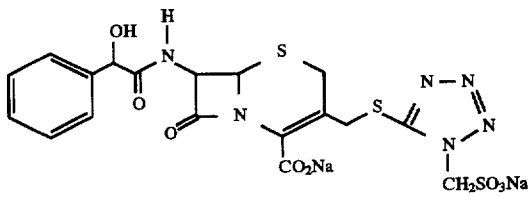

The disodium salt of cefonicid is only moderately stable at room temperature, requiring refrigeration and special handling for transport and storage.

It was later discovered that the monosodium salt of cefonicid was an unexpectedly more stable form of the antibiotic as compared to the disodium salt. Thus, the antibiotic in its monosodium salt form could be stored for longer periods of time without refrigeration than the disodium salt. This invention is described in U.S. Pat. No. 4,576,937. The monosodium salt of cefonicid is not a commercially practical antibiotic unless administered with a companion buffer.

Cefonicid is an extremely water soluble cephalosporin between pH 1 to 10 due to the presence of the sulfonic acid moiety. The molecule is extremely difficult, and for all practical purposes impossible, to extract into an organic phase. Thus, isolation by conventional methods of solvent extraction are difficult. Consequently, isolation and purification of cefonicid at present requires lengthy and cumbersome steps for sample preparation, purification by chromatography and final isolation by lyophilization. The benzathine salts of other cephalosporin antibiotics have been described in U.S. Pat. No. 4,737,492 and the European Patent Application EP 0399094. U.S. Pat. No. 4,737,492 describes the benzathine salt of cefamandole for use in opthamalic compositions. European Patent Application EP 0399094 describes an improved process for the preparation of ceftriaxone. The formation of the benzathine salt and crystallization of such an extremely water soluble cephalosporin as cefonicid and the resulting improvement in ease of sample isolation and purification of cefonicid is not known in the prior art.

SUMMARY OF THE INVENTION

One object of this invention is to provide an improved process for isolation and purification of cefonicid.

Another object of this invention is to provide a stable composition and pharmaceutically viable form of cefonicid which allows for easier storage and handling.

One feature of this invention is a novel salt form of cefonicid.

DETAILED DESCRIPTION OF THE INVENTION

Cephalosporins having acidic groups that impart a high degree of water solubility to the molecule are difficult to isolate via conventional methods of solvent extraction. Cefonicid, in particular, is extremely water soluble due to the presence of a sulfonic acid moiety. It has now been discovered that cefonicid may be readily isolated and/or purified by forming a benzathine salt of the free acid. This salt is readily isolated in a crystalline form via conventional filtration. Thus, the benzathine salt facilitates isolation of cefonicid.

The benzathine salt is the first known crystalline form of cefonicid. It has also been discovered that this form is more stable than the disodium salt of cefonicid and that crystallization of the salt yields a product of high purity. The enhanced stability allows for transport of cefonicid without refrigeration or special handling during storage. More importantly, this crystalline product need not be isolated via chromatography, thus eliminating a cumbersome process work-up step. This cefonicid salt is easily isolated via filtration. The salt can also be convened to Na, K, or Ca salts via conventional salt transfer means such as cation exchange resins or by addition of an organic solvent soluble salt of an organic acid or a strong base.

As used herein, benzathine refers to dibenzylethylene diamine. Cefonicid refers to 7-D-mandelamido-3-(1-sulfomethyltetrazol-5-yl)-thiomethyl-3-cephem-4-carboxylic acid, or [6R-[6.alpha., 7.beta.(R*)]]-7-9-hydroxyphenylacetyl)amino-8-oxo-3-[[[1-(sulfomethyl)-1H-tetrazol-5-yl]thio]methyl]-5-thia-1-azabicyclo[4.2.0]oct-2-ene-2-carboxylic acid as the free acid or in a suitable salt form.

Methods for preparing cefonicid are disclosed in U.S. Pat. No. 4,576,937 and WO 92/17600 (PCT/US92/02781) which are incorporated herein by reference.

According to this invention, salts of this compound which produce a crystalline form of cefonicid are produced by reaction with benzathine. Typically an aqueous solution of cefonicid, either as a crude reaction mixture, an impure product or in a purified state, is adjusted to pH 2.0–8.0, more preferably pH 5.0–6.0, with any conventional organic or inorganic acid or base, such as hydrochloric acid, acetic acid, or an alkali hydroxide. Preferably then, inorganic salts such as NaCl are removed to avoid precipitation of solvent insoluble benzathine salts. The solution is then treated with a suitable organic solvent. Suitable organic solvents are organic solvents with a water solubility of generally 0.5% or greater. Examples include acetone, acetonitrile, dimethyl sulfoxide, dimethyl formamide, dioxane, ethyl acetate, methylethylketone, methanol, ethanol, isopropyl alcohol, tetrahydrofuran, toluene or methylisobutylketone, preferably methanol. Treatment with a suitable organic solvent supports crystallization of the benzathine cefonicid rather than formation of an amorphous gummy product. A suitable salt of N,N'-dibenzylethylenediamine, such as the diacetate salt, is then added in about 0.5 to 4, preferably about 1 to about 3, most preferably about 2.2 to about 2.5 molar equivalents. The solution is then mixed for a period of time sufficient for crystallization, typically several hours, usually 3 to 5 hours. White crystals of the cefonicid salt are then isolated by filtration. Typically the crystals will have a melting point between about 189° to about 198° C.; preferably between 191° to 198° C., most preferably between 195° to 198° C. for a pure sample. Analysis indicates about a 1:1 mixture of benzathine to cefonicid.

The benzathine cefonicid may be converted to sodium cefonicid in powder or crystal form via conventional salt interchange by converting the benzathine cefonicid to the free acid and treating the free acid with cation exchange resins or organic solvent soluble salts of organic acids such as sodium-2-ethylhexanoate, sodium lactate, and sodium acetate or strong bases such as sodium hydroxide or sodium methoxide and the like. For instance the benzathine salt of cefonicid can be suspended in ethyl alcohol, methyl alcohol, water or other protic solvents, preferably ethyl alcohol, at a ratio of benzathine salt to solvent ranging from about 1:5 to about 1:30 w/vol, preferably ranging from 1:10 to 1:20 w/vol. While the suspension is stirring, a strong acid or a strongly acidic cation exchange resin is added to liberate the cefonicid free acid. For instance, a strongly acidic cation exchange resin, such as Amberlyst®.15, Amberlite® IR-120, Duolite® ES-280, Thermax® T-63, and Thermax® T-54, is added at a ratio of benzathine salt to resin ranging from about 1:1 to about 1:10 w/w, preferably ranging from 1:1.5 to 1:3 w/w. This mixture is stirred for several hours at 5°-35° C. until the benzathine salt of cefonicid dissolves and a clear solution results. The resin is filtered off and the filtrate is titrated to a pH of about 2–3 to form the monosodium salt and a pH of 5–6, to form the disodium salt. Organic solvent soluble sodium salts such as sodium-2-ethylhexanoate, sodium tactate, or sodium acetate or a strong base such as aqueous sodium hydroxide or sodium alkoxide are suitable. The salt formation is typically conducted at a temperature of less than 15° C., preferably 5°-10° C. The solid sodium salt of cefonicid precipitates from the solution and after several hours of stirring at a temperature of less than 15° C., preferably 5°-10° C., the product is filtered off. If the benzathine cefonicid is suspended in a polar solvent in which the sodium salt of cefonicid is soluble, such as water or methanol, then the sodium cefonicid will not precipitate but rather the solution will require lyophilization or co-precipitation with an organic solvent of lower polarity such as isopropanol. In so doing, cefonicid sodium need not be isolated via chromatography, thus eliminating a cumbersome work up.

Pharmaceutical compositions having antibacterial activity which comprises a pharmaceutically acceptable carrier containing an active but non-toxic quantity of the benzathine salt of cefonicid are also a part of this invention. Suitable solid and liquid carriers are found, for instance, in REMINGTON'S PHARMACEUTICAL SCIENCES, Gennaro, A. (ed.), Merck Publishing Co., Easton, Pa., 1985 and SPROUL'S AMERICAN PHARMACY, Dittert, L. (ed.), J. B. Lippincott Co., Philadelphia, Pa. 1974, which are incorporated herein by reference. Liquid carriers include syrup, peanut oil, soybean oil, olive oil, glycerin, propylene glycol, fatty acids and water and suitable combinations thereof. Solid carriers include starch, lactose, calcium sulfate dihydrate, tera alba, magnesium stearate or stearic acid, talc, pectin, acacia, agar or gelatin. Suitable excipients, such as melting agents, dispersing agents, emulsifiers and buffering agents may be added to enhance or stabilize the composition or to facilitate preparation of the composition. The administration may be by subcutaneous, intraperitoneal or intramuscular injection, orally or topically as in an opthamalic composition.

The injection, being either intramuscular, subcutaneous or intraperitoneal, of suitably prepared sterile suspensions containing an effective, non-toxic amount of the benzathine salt of cefonicid is the preferred route of administration. Aqueous-based pharmaceutical compositions with a suspending agent are preferred. Suitable carriers for injection, either intramuscular, subcutaneous or intraperitoneal, and oral administration include water, 5% dextrose in water, saline, tragacanth 1.25%, guar gum 0.5%, and sodium carboxymethylcellulose 2.5%.

Alternately, the compound may be encapsulated, tableted, or prepared in an emulsion or syrup for oral administration. Pharmaceutical preparations are made following conventional techniques of pharmacy involving milling, mixing, granulating, and compressing, when necessary, for tablet forms; or milling, mixing and filling for hard gelatin capsule forms. The amount of solid carrier varies but, preferably will be between about 20 mg to about 1 g per dosage unit. When a liquid carrier is used, the preparation will be in the form of a solution, syrup, elixir, emulsion or an aqueous suspension. Such a liquid formulation may be administered directly p.o. or filled into soft gelatin capsules.

Suppositories for rectal administration of the drug can be prepared by mixing the drug with a suitable non-irritating excipient such as coca butter and polyethylene glycols which are solid at ordinary room temperature but liquid at rectal temperature and will therefore melt and release the drug.

The benzathine salt of cefonicid may also be converted to the sodium salt which can be dissolved in a sterile aqueous pharmaceutical carrier and used for intravenous injection as is well known in the art.

The benzathine salt of cefonicid is formulated and administered in a similar manner to other injectable cephalosporins. However, benzathine cefonicid is insoluble in aqueous pharmaceutical vehicles and may require addition of suspending agents to the vehicle. The dosage regimen comprises administration, preferably by intramuscular, subcutaneous or intraperitoneal injection, of an active but non-toxic quantity of the compound selected from the dosage unit range of from about 100 to about 1000 mg with the total daily dosage regimen being from about 100 mg to about 6 g. The anticipated adult daily dosage regimen will be about from 500 mg to about 2 g., preferably about 1 g. The precise dosages are dependent upon the age and weight of the subject and on the infection being treated and can be determined by those skilled in the art.

The cationic resins referred to herein, such as Amberlyst® 15, Amberlite® IR-120, Duolite® ES-280 and Thermax® T-63 and T-54, are sulfonylated polystyrene type, sulfonic acid resins. Amberlyst® and Amberlite® are registered trademarks of Rohm and Hass Corporation, Philadelphia, Pa. 19105. Duolite® is a registered trademark of Diamond Shamrock Company, Irving, Tex. Thermax® is a registered trademark of Tulsion, Novi, Mich.

The following Examples are purely illustrative and are provided to teach how to make and use the compound of the present invention, but are not intended to limit the scope of the present invention in any manner.

EXAMPLE 1

Preparation of N,N'-Dibenzylethylene diamine-7-[(hydroxyphenylacetyl)amino-8-oxo-3-[[[1- (sulfomethyl)-1H-tetrazol-5-yl]thio]methyl]-5-thia-1-azabicyclo[4.2.0] oct-2-ene-2-carboxylate To a stirred solution of cefonicid (5.76 g, 9.8 mmol) in water (6.3% w/w), at pH 5–6 and ambient temperature, methanol (50 ml) was added, followed by a suspension of N,N-dibenzylethylene diamine diacetate (8.6 g, 24 mmol) in methanol (50 ml). The reaction mixture was stirred for 3 h at 20°–25° C., resulting in formation of a white solid. The reaction mixture was cooled to 10°–15° C. and filtered. The white solid was washed with water (3×15 ml) and methanol (3×10 ml). The solid was dried at 30°–35° C. under vacuum. (7.63 g, 99.4% yield). The melting range of the crystals was 191°–193° C. Washed salt with water (50 ml×2) followed by methanol (120 ml) to yield a product with a melting range of 195°–198° C. Elemental Analysis ($C_{34}H_{38}N_8O_8S_3$) calcd: C, 52.16; H, 4.89; N, 14.31; S, 12.26. found: C, 52.06; H, 4.89; N, 14.01; S, 12.27.

EXAMPLE 2

Preparation of 7-[(Hydroxyphenylacetyl)amino]-8-oxo-3-[[ [1-(sulfomethyl)-1-H-tetrazol-5-yl]thio]methyl]-5-thia-1-azabicyclo[4.2.0]oct-2-ene-2-carboxylic acid, disodium salt To a stirred suspension of cefonicid benzathine (2.5 g, 3 mmol) in ethyl alcohol (35 ml) at 5°–10° C. was added Amberlyst®.15 resin (6.25 g). The mixture was stirred for 2 h until cefonicid benzathine dissolved and a clear solution resulted. The resin was filtered and sodium methoxide solution at 5°–10° C. was added to the clear ethyl alcohol filtrate until the pH reached 5.5. A white solid was precipitated. This suspension was stirred for 2 h at 5°–10° C. and the solid cefonicid sodium was filtered and dried (1.78 g, 95% yield).

What is claimed is:

1. N,N'-Dibenzylethylene diamine -7-[(hydroxyphenylacetyl)amino-8-oxo-3-[[[1-(sulfomethyl)-1H-tetrazol-5-yl]thio]methyl]-5-thia-1-azabicyclo[4.2.0] oct-2-ene-2-carboxylate.

2. The compound of claim 1 having a melting point of about 189°–198° C.

3. A pharmaceutical composition comprising the compound of claim 1 and a pharmaceutically acceptable carrier.

4. A pharmaceutical composition of claim 1 wherein such composition is a solid powder or crystalline composition.

5. A method for treating bacterial infections comprising administering the compound of claim 1.

6. A process for preparing the benzathine salt of cefonicid which comprises treating an aqueous solution or suspension of cefonicid with an organic solvent and N,N'-dibenzylethylenediamine.

7. The process according to claim 6 wherein the aqueous solution is treated with acetone, ethyl acetate, methylethylketone, methyisobutylketone, methanol, ethanol, propanol or isopropanol.

8. The process of claim 6 wherein the aqueous solution is between about pH 2 and 8.

* * * * *